US007983457B2

(12) United States Patent
Toth et al.

(10) Patent No.: US 7,983,457 B2
(45) Date of Patent: Jul. 19, 2011

(54) METHOD AND SYSTEM FOR AUTOMATICALLY DETERMINING REGIONS IN A SCANNED OBJECT

(75) Inventors: Thomas Louis Toth, Brookfield, WI (US); Michael Patrick Daly, LaGrange, IL (US)

(73) Assignee: General Electric Company, Schenectady, NY (US)

( * ) Notice: Subject to any disclaimer, the term of this patent is extended or adjusted under 35 U.S.C. 154(b) by 825 days.

(21) Appl. No.: 11/287,029

(22) Filed: Nov. 23, 2005

(65) Prior Publication Data

US 2007/0116337 A1 May 24, 2007

(51) Int. Cl.
*G06K 9/00* (2006.01)
*A61B 6/00* (2006.01)

(52) U.S. Cl. .......................................... 382/128; 378/16

(58) Field of Classification Search .......... 382/128–132; 378/4, 16, 37, 108, 118; 128/922; 250/455
See application file for complete search history.

(56) References Cited

U.S. PATENT DOCUMENTS

| | | | |
|---|---|---|---|
| 5,379,333 A * | 1/1995 | Toth .............................. | 378/16 |
| 5,400,378 A * | 3/1995 | Toth .............................. | 378/16 |
| 6,246,784 B1 | 6/2001 | Summers et al. | |
| 6,345,112 B1 | 2/2002 | Summers et al. | |
| 6,369,389 B1 * | 4/2002 | Berlad et al. ............. | 250/363.07 |
| 6,492,812 B1 | 12/2002 | Debbins et al. | |
| 6,748,044 B2 | 6/2004 | Sabol et al. | |
| 6,816,571 B2 * | 11/2004 | Bijjani et al. .................. | 378/57 |
| 6,904,127 B2 * | 6/2005 | Toth et al. ..................... | 378/110 |
| 6,990,171 B2 * | 1/2006 | Toth et al. ........................ | 378/16 |
| 7,031,425 B2 * | 4/2006 | Hsieh et al. ....................... | 378/5 |
| 7,042,977 B2 * | 5/2006 | Dafni ............................... | 378/16 |
| 2002/0054662 A1 | 5/2002 | Verdonck et al. | |
| 2002/0063560 A1 | 5/2002 | Debbins et al. | |
| 2002/0075997 A1 | 6/2002 | Unger et al. | |
| 2004/0052328 A1 | 3/2004 | Sabol et al. | |
| 2004/0101087 A1 | 5/2004 | Hsieh et al. | |
| 2004/0101179 A1 | 5/2004 | Suryanarayanan et al. | |
| 2005/0089137 A1 | 4/2005 | Toth et al. | |
| 2005/0113671 A1 | 5/2005 | Salla et al. | |
| 2005/0259882 A1 * | 11/2005 | Dewaele ........................ | 382/243 |
| 2007/0171225 A1 * | 7/2007 | Haex et al. ..................... | 345/473 |

FOREIGN PATENT DOCUMENTS

| | | |
|---|---|---|
| EP | 1205768 A2 | 5/2002 |
| WO | WO-9318470 A1 | 9/1993 |
| WO | WO-2005088520 A1 | 9/2005 |

OTHER PUBLICATIONS

Valentin, "Basic Anatomical & Physiological Data for Use in Radiologic Protection", Annals of the ICRP, vol. 32, Issues 3-4, Sep.-Dec. 2002, pp. 1-277.*
Written Opinion; Netherlands; Application NL 1032927; Aug. 3, 2009; 9 pages.
Translation of Chinese Second Office Action; 5 pgs.

* cited by examiner

*Primary Examiner* — Vu Le
*Assistant Examiner* — Andrae S Allison
(74) *Attorney, Agent, or Firm* — Dean Small; The Smalll Patent Law Group

(57) ABSTRACT

A method and system for automatically determining regions in scanned object are provided. The method includes performing a scout scan of an object and automatically determining regions within the object based on attenuation information from the scout scan.

24 Claims, 4 Drawing Sheets

METHOD AND SYSTEM FOR AUTOMATICALLY DETERMINING REGIONS IN A SCANNED OBJECT

BACKGROUND OF THE INVENTION

This invention relates generally to methods and systems for imaging, and more particularly to methods and systems for automatically determining regions in a scanned object, particularly using medical imaging systems.

Imaging systems are typically used to scan objects, and often are used to identify regions of interest within the objects. For example, in certain known computed tomography (CT) imaging systems, an x-ray source transmits x-ray beams through an object of interest. The x-ray beams pass through the object being imaged, such as a patient. The beams, after being attenuated by the object, impinge upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. Attenuation measurements from the detectors are acquired separately for each detector element and collectively define a projection data set or transmission profile.

The x-ray source and the detector array may be rotated on a gantry within an imaging plane around the object to be imaged such that the angle at which the x-ray beam intersects the object constantly changes. A group of x-ray attenuation measurements (e.g., projection data set), from the detector array at one gantry angle is referred to as a "view". A "scan" of the object comprises a set of views made at different gantry angles, or view angles, during one revolution of the x-ray source and detector. The projection data sets are processed to construct images that correspond to two-dimensional slices taken through the object at various angles. One exemplary method for forming an image from a projection data set is referred to as a filtered back projection technique.

Obtaining an optimum scan, for example, an optimum CT scan at the lowest possible dose relies on patient dependent information. X-ray flux management systems are known for obtaining patient dependent information in order to determine various operating parameters for scanning, such as the proper tube current, bowtie filter, and patient centering. Other information such as where to scan the patient must be determined by the technologist and be manually entered into the system in some manner. Generally, this manual operation is performed using a graphic Rx display by marking locations with a mouse and cursor on a scout image. A scout image is a radiographic projection image of the object that is obtained with the x-ray tube at a fixed stationary position while the object is translated in the Z axis. Marking locations on the scout image can be a very time consuming and complex process that is dependent on the experience of the technologist. This not only reduces scanning throughput, but can increase errors, for example, based on errors in the judgment of the technologist.

In addition, many potential dose management features are currently not practical or would be awkward and time consuming for the user because of the need to identify the required anatomic information. For example, dose reduction for dose sensitive organs is currently not available on CT scanners. One reason is that the technologist must identify and manually mark the location of sensitive organs such as breast, thyroid, eyes, uterus, etc. on a graphic Rx display. Size adjusted noise index and patient centering are ideally determined using the mean scout projections that are averaged over only the trunk of the body (top of lungs to the hips). Results can be adversely affected if portions of the neck or legs are included in the average, which can occur using known manual marking methods. Further, the radiologist may want to use different scan parameters for different regions of a helical scan. For example, in a chest-abdomen protocol a higher noise index may be desired for the lungs because nodule lesions have more contrast compared to lesions in the liver. Different regions (such as the lungs) are manually identified on the graphic Rx display by a technologist and can result in including more anatomy than needed for the region of clinical interest, thereby increasing patient dose and tube loading.

Further, some regions of the anatomy may require special compute intensive image reconstruction pre-processing correction steps. For example, the head requires a correction to compensate for bone beam hardening and detector spectral errors that would otherwise produce artifacts in the presence of bone in the skull. This correction is very compute intensive as the computations require an iterative approach. Image reconstruction times would take too long if this correction were applied for every image. Some hospitals perform trauma scans in one pass that include both the head and body. In this case, correction may be performed on data that does not need the correction because the regions are not properly identified due to technologist errors in the manual identification process. Also, Effective Dose is a common metric that permits estimating biological risk and allows doses to be compared from different imaging modalities. There are many known ways to calculate Effective Dose, but all of the methods need to know the organs that have been exposed to x-ray so that the appropriate organ doses can be determined. Accurate organ doses require lengthy Monte Carlo simulations. To speed up calculations, organ doses can be characterized on an anthropomorphic phantom and deterministic equations developed to translate the exposure of a given body region to an organ dose estimate. Again, manual determinations and identification of the organs adds time to this process.

Thus, known methods for identifying regions in a scanned object are often time consuming and susceptible to human error. Further, this manual identification also increases the time and complexity of processing using the manually identified information.

BRIEF SUMMARY OF THE INVENTION

In accordance with one embodiment, a method for controlling an imaging system is provided. The method includes performing a scout scan of an object and automatically determining regions within the object based on attenuation information from the scout scan.

In accordance with another embodiment, a method for determining the location of regions in a human scanned with a medical imaging system is provided. The method includes performing a scout scan of the human with the medical imaging system and automatically determining anatomic locations within the human using the scout scan.

In accordance with yet another embodiment, a medical imaging system is provided that includes a scanner configured to perform a scout scan and an anatomy determination unit configured to automatically determine anatomic locations within a human based on the scout scan.

DETAILED DESCRIPTION OF THE INVENTION

Figure 1:
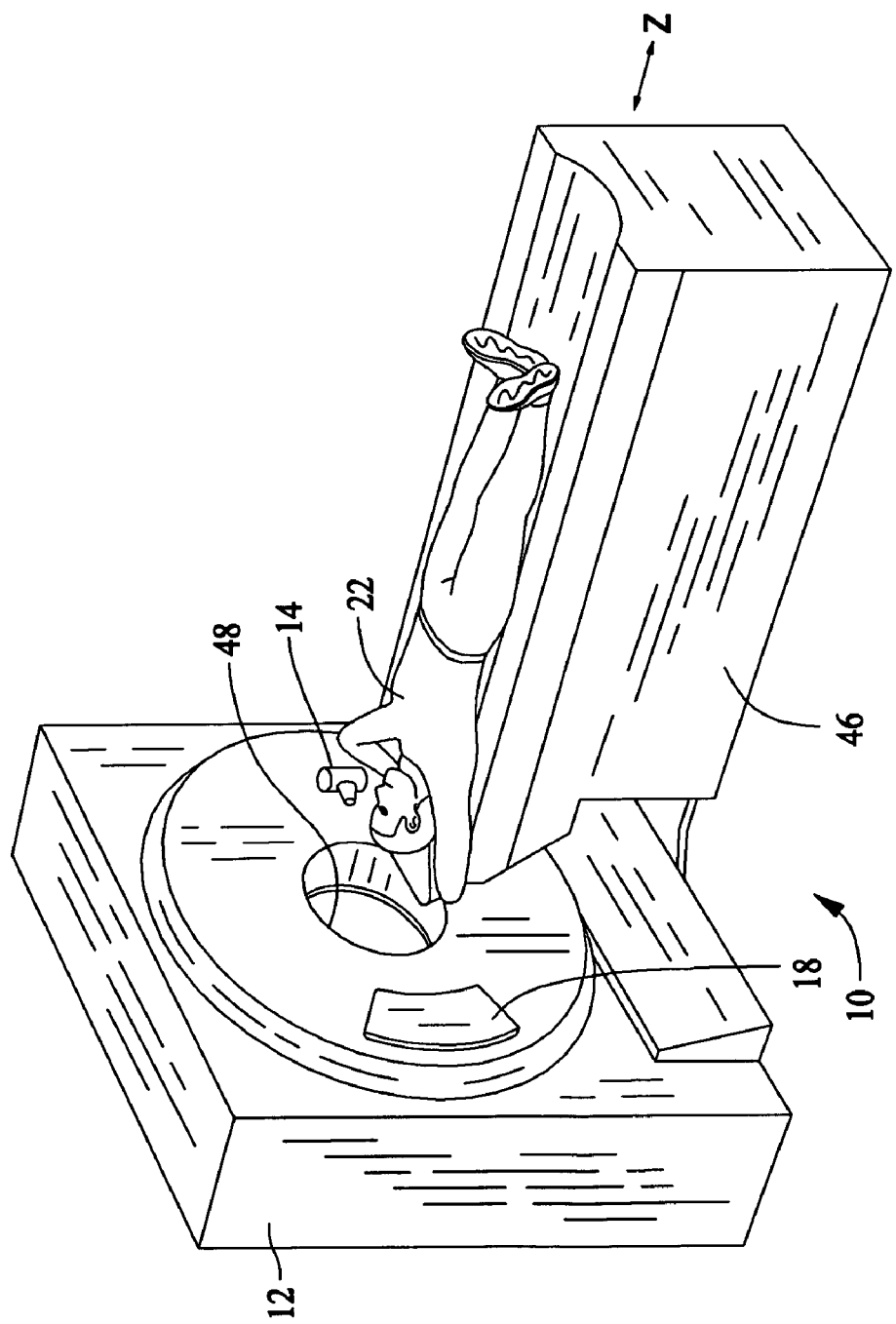
FIG. 1 is a perspective view of an exemplary imaging system operated in accordance with an embodiment of the invention.
Figure 2:
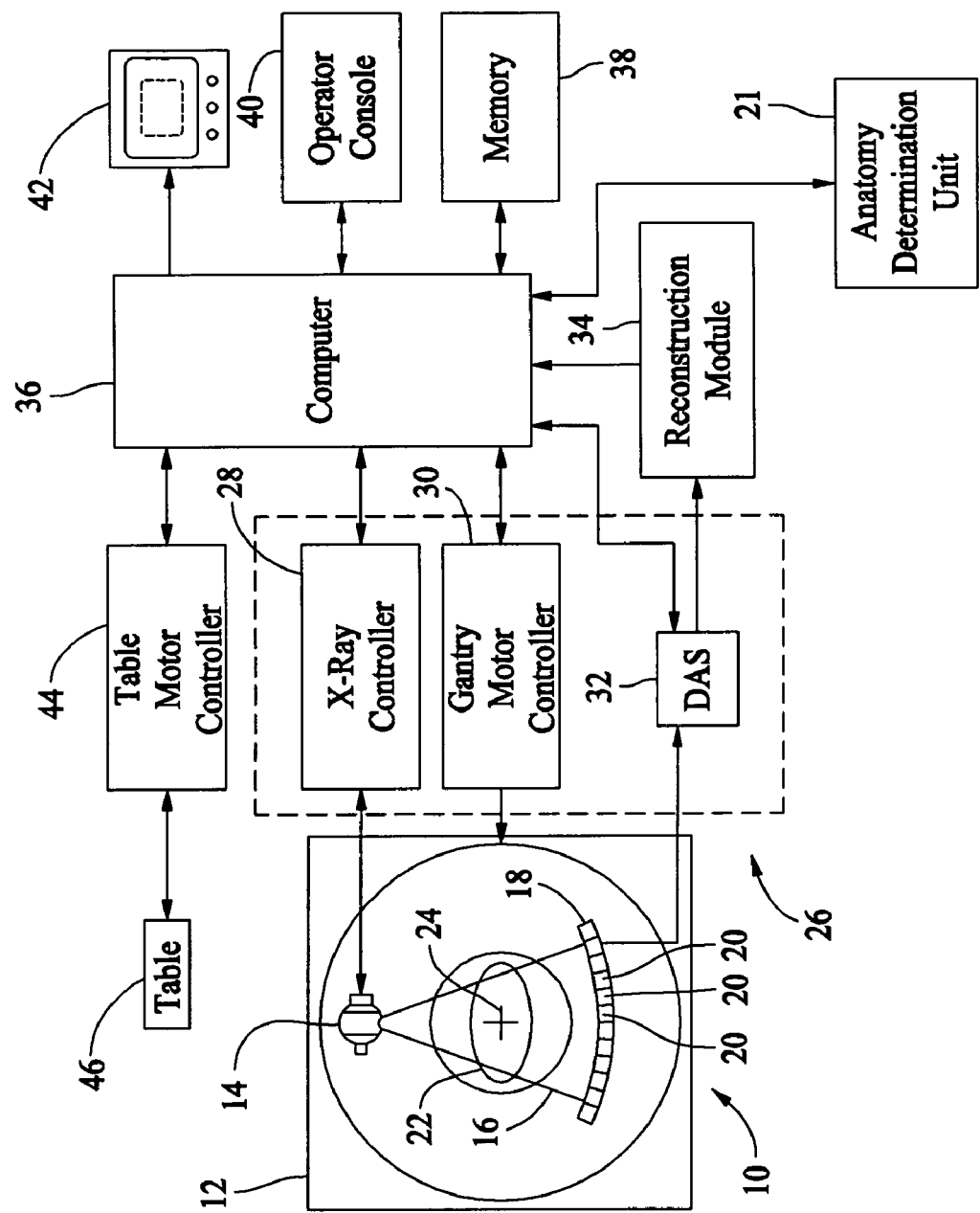
FIG. 2 illustrates a block diagram of the imaging system illustrated in FIG. 1.

FIG. 1 is a perspective view of an exemplary imaging system 10. FIG. 2 is a schematic block diagram of the imaging system 10 (shown in FIG. 1). In an exemplary embodiment, the imaging system 10 is a single modality imaging system, for example, a computed tomography (CT) system. However, it should be understood that the various embodiments may be implemented in connection with imaging systems having more than one imaging modality (i.e., multi-modality imaging systems). Additionally, although the various embodiments may be described in connection with a particular imaging modality, for example, CT imaging, different imaging modalities both medical and non-medical may be used, for example, Positron Emission Tomography (PET), and in general any type of x-ray or nuclear imaging.

Referring now specifically to FIGS. 1 and 2, a computed tomography (CT) imaging system 10 is shown that includes a gantry 12 for a CT scanner. The gantry 12 includes an x-ray source 14 that projects a beam of x-rays 16 toward a detector array 18 on the opposite side of the gantry 12. The detector array 18 is formed by detector elements 20 (e.g., a plurality of detector rows) that together sense the projected x-rays that pass through an object 22, for example a medical patient. The detector array 18 may be fabricated in a single slice or multi-slice configuration. Each detector element 20 produces an electrical signal that represents the intensity of an impinging x-ray beam and hence the attenuation of the beam as the beam passes through the object 22. During a scan to acquire x-ray projection data, the gantry 12 and the components mounted thereon rotate about a center of rotation 24, which may define an examination axis.

The rotation of the gantry 12 and the operation of the x-ray source 14 are controlled by a control mechanism 26 of the imaging system 10, which in one embodiment is a CT imaging system. The control mechanism 26, in an exemplary embodiment, includes an x-ray controller 28 that provides power and timing signals to the x-ray source 14 and a gantry motor controller 30 that controls the rotational speed and position of the gantry 12. A data acquisition system (DAS) 32 of the control mechanism 26 samples data (e.g., analog data) from the detector elements 20 and converts (or conditions) the data to digital signals for subsequent processing. The DAS 32 outputs projection data sets including attenuation measurements obtained at particular gantry rotation angles, for example, from a scout scan. A group of projection data sets form a complete scan of object 22. A reconstruction module 34 receives sampled and digitized x-ray data from the DAS 32 and performs image reconstruction as explained below. The reconstruction data sets output by the reconstruction module 34 are provided as an input to a computer 36 or other processing unit that stores the reconstruction data sets in a memory 38. The reconstruction data sets may represent volumetric data sets and/or image slices through the object 22. The computer 36 also receives commands and scanning parameters from an operator via an operator console 40 that may include one or more use inputs, for example, a keyboard (not shown). An associated display, for example, a cathode ray tube display 42 allows the operator to observe reconstructed image and other data from the computer 36. Further, the operator supplied commands and parameters are used by the computer 36 to provide control signals and information to the DAS 32, the x-ray controller 28 and the gantry motor controller 30. In addition, the computer 36 operates a table motor controller 44 that controls a motorized table 46 to position the object 22 in the gantry 12. In particular, the table 46 moves portions of the object 22 through a gantry opening 48.

In one embodiment, the computer 36 includes a read/write device (not shown), for example, a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, a CD-ROM, a DVD or an other digital source such as a network or the Internet, as well as yet to be developed digital means. In another embodiment, the computer 36 executes instructions stored in firmware (not shown). The computer 36 is programmed to perform functions as described herein, and as used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein.

A unit to determine a particular region of the object 22 is communicatively coupled to the computer 36, and which in one exemplary embodiment is an anatomy determination unit 21. Although the anatomy determination unit 21 is illustrated as a separate component, it should be understood that that functions performed by the anatomy determination unit 21 may be incorporated into functions performed by, for example the computer 36. Accordingly the anatomy determination unit 21 may be embodied in a software code segment executing on a multifunctional processor or may embodied in a combination of hardware and software.

Additionally, although described in a medical setting, it is contemplated that the embodiments of the invention may be implemented in connection with other imaging systems including industrial imaging systems such as, for example, a baggage scanning CT system typically used in a transportation center, for example, an airport or a rail station.

Figure 3:
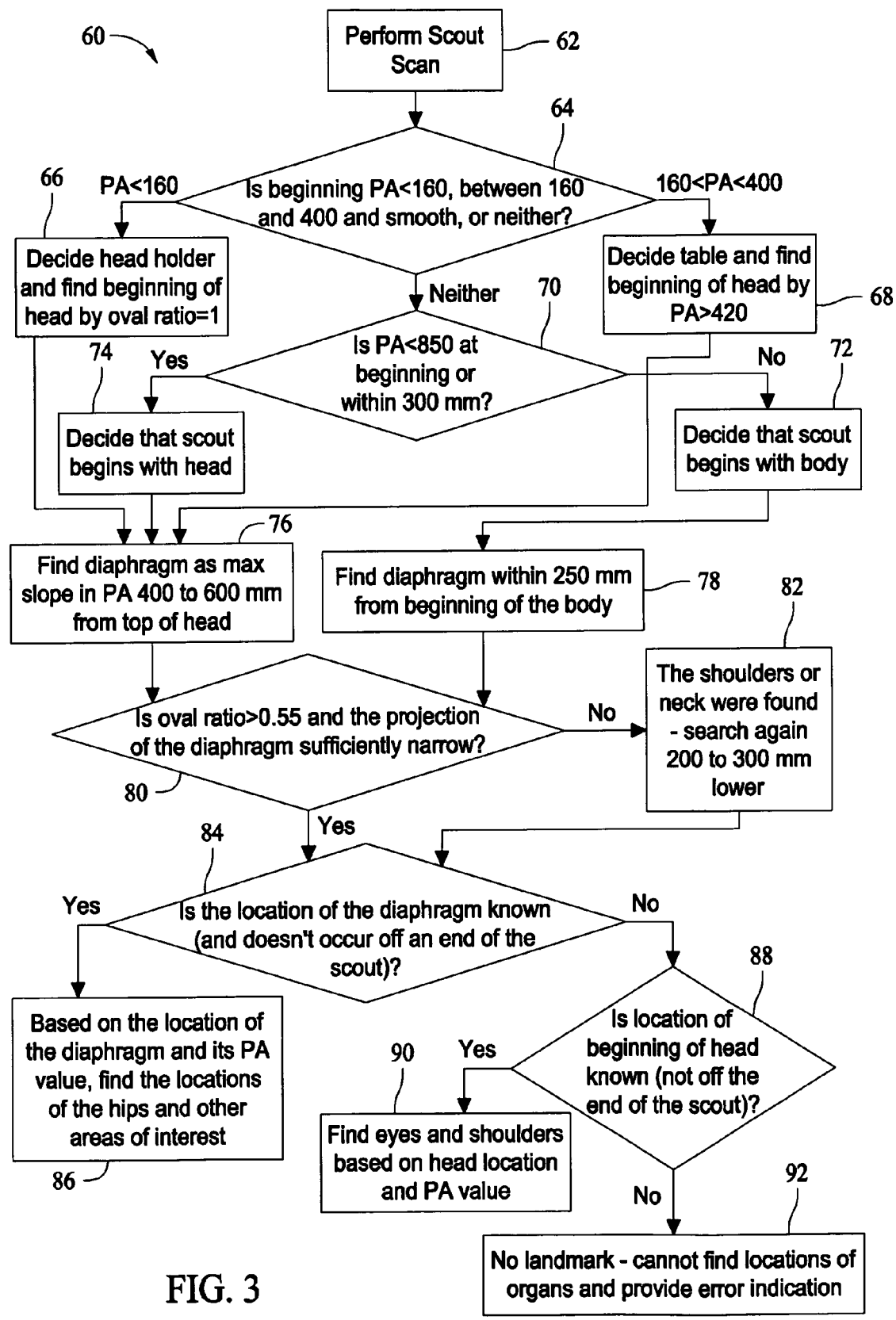
FIG. 3 is a flow chart of a method to automatically determine regions in a scanned object in accordance with an embodiment of the invention.

Various embodiments provide automatic determination of regions of an object based on a preliminary scan. Using various thresholds determined by projection area or oval ratio, the location of at least one landmark within the object is determined, and from that, other regions identified. FIG. 3 is a flow chart setting forth an exemplary method 60 performed by the anatomy detection unit 21 to automatically determine anatomical regions or landmarks within a human body. It should be noted that the method 60 may be modified and used in connection with scans of objects other than human bodies and with imaging systems other than medical imaging systems.

Figure 4:
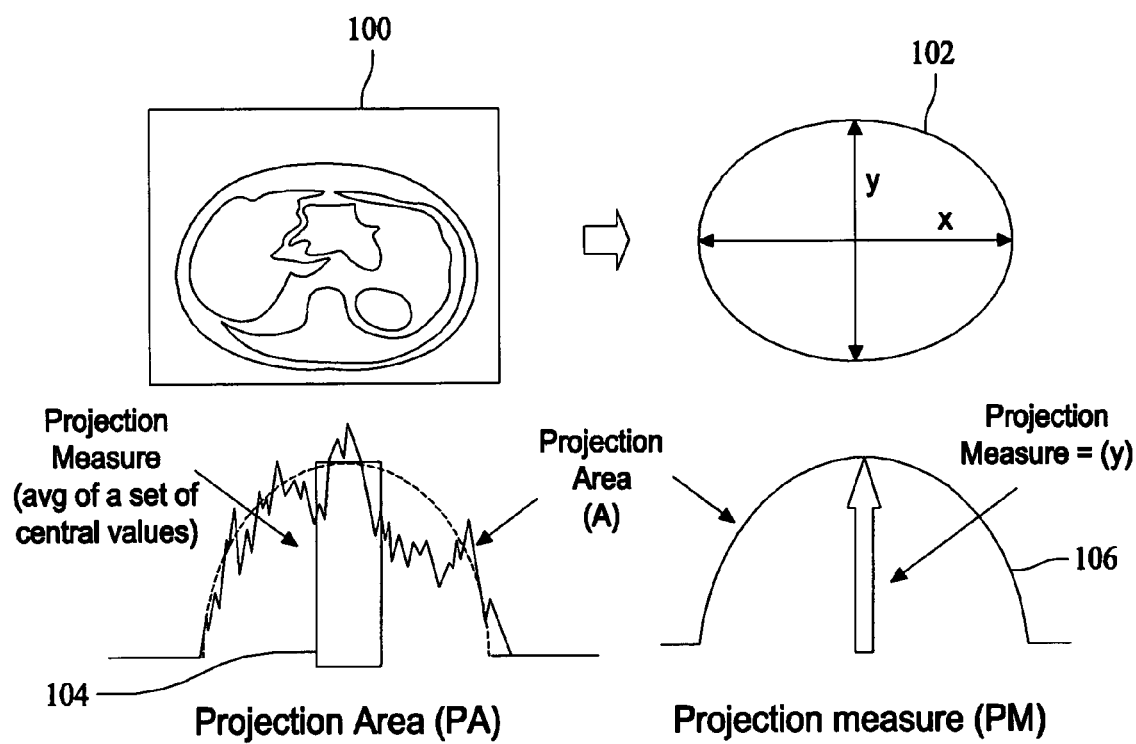
FIG. 4 is a diagram illustrating a projection area determined in accordance with an embodiment of the invention.

Specifically, the method 60 illustrates an automatic anatomy determination process for use in connection with a medical imaging system, and more particularly, a CT imaging system. In particular, at 62, a scout scan, which may be either a lateral or anterior/posterior (A/P) scout scan is performed as is known to generate a scout image, which is essentially an attenuation image. The projection area (PA) and oval ratio (OR) of the scout scan is then used to identify anatomical regions or landmarks within the body. It should be noted that in an exemplary embodiment, the cross-section of a human body 100 as shown in FIG. 4 can be considered as an ellipse 102 having an elliptical cross-section with dimensions x and y. A patient projection is comprised of a set of individual detector channel measurements. The channel measurements represent the x-ray transmission along a line through the patient. The transmission values are processed to represent attenuation units related to the effective μ and length of the object along the transmission path. The summation of the individual channel measurements is the PA 106. A set of the highest value measurements in the projection is referred to as a projection measure (PM) 104. The oval ratio is the x/y ratio of the effective ellipse. The x dimension for the oval ratio is determined using the equation for the area of an ellipse where the PA 106 is the ellipse area and the PM 104 is the y axis of the ellipse. Essentially, each slice from the scout scan performed by the CT scanner of the imaging system is a projection. The set of projections produce the scout image.

Once the attenuation PA for each projection or sample along the entire scan is determined, for example, for each slice along the scan, then a determination is made at 64 as to whether the attenuation for the PA at initially at the start of the scan is less than a first threshold or greater than the first and less than a second threshold. For example, for a CT scan, a determination is made at 64 as to whether the attenuation for the initial PA is less than 160 or between 160 and 400. It should be noted that the values, including the attenuation values for the different thresholds described herein may be changed or modified as desired or needed (e.g., based on the object to be scanned). If the attenuation is less than 160 then at 66 the start location of the scan is identified as a head holder of the CT scanner, and more particularly, the head holder of the scan bed for supporting a human head. This identification may be based on, for example, the distribution of an average projection area of a head holder. The beginning of the head is then located by finding a circular object, for example, a point where an oval ratio equals one. If the ratio is not one, then the object is not circular and not identified as the start of the head. The oval ratio is the ratio of the length and width of the scanned body, for example, the x and y dimensions as shown in FIG. 4.

If a determination is made at 64 that the initial PA attenuation is between 160 and 400 (and the attenuation is substantially smooth or flat over that region), then at 68 the start location of the scan is identified as the table of the CT scanner and the beginning of the head is determined by locating the point in the scout scan where the PA attenuation is greater than a third threshold, in this example, where the PA attenuation is greater than 420. The identification of the table may be based on, for example, the distribution of an average projection area of a scanner table. It should be noted that substantial flatness is identified, for example, when the standard deviation occurs in a predetermined number, for example, in the first ten data points measured in the scout scan.

If the initial PA attenuation is not less than the first threshold or between the first and second threshold, then the scan start location is identified as some point within the object and a determination is made at 70 as to whether the initial PA attenuation is less than a fourth threshold within a predetermined distance (e.g., length) along the scanned object. In this example, a determination is made at 70 as to whether the initial PA attenuation is less than 850 at any point within about 300 millimeters of the initial scan point. If the initial PA attenuation is not less than the fourth threshold at a point along the predetermined distance, then at 72 the start location of the scan is identified as beginning within the body of the object. If the initial PA attenuation is less than the fourth threshold at a point along the predetermined distance, then at 74 the start location of the scan is identified as the head of the object.

Essentially, if at 64 a determination is made that the scout scan started at an unoccupied portion of the table, then a determination is made as to where a first significant increase in PA attenuation, for example, above 400, occurs, which identifies the beginning of the head. If the head holder is identified as the scout start scan point, then the first point at which the oval ratio is substantially one or greater is determined and identified as the start of the skull. If a determination is made that the scout scan started at some point along the object, then a determination is made as to whether the scan started at the head or a part of the body by determining if there is a substantial decrease in the magnitude of the attenuation at the start of the scout scan, such magnitude level being low enough to be identified as the neck of the object.

After determining or identifying the location within the body of the starting point of the scout scan, in an exemplary embodiment, a determination is then made to identify the diaphragm of the body. The diaphragm region is generally characterized by a steep increase in the attenuation in the projection area. For example, once the location for a maximum PA attenuation is determined, a determination is made as to whether the distance is reasonable based on, for example, the distance from the start of the body where the maximum PA attenuation is determined. If the head is identified, this distance to identify the maximum PA attenuation, and more particularly, the maximum slope, is limited to a predetermined distance from the top of the head, otherwise the distance is limited to a lesser amount. In particular, and with reference again to FIG. 3, if the beginning of the head is located at 66 or 68, or if a determination has been made at 74 that the scout scan started at the head, then at 76 the point at a predetermined distance from the top of the head where the maximum slope of the PA attenuation occurs is identified. In this example, a determination is made at 76 as to the point within about 400 mm to about 600 mm from the identified top of the head where the PA attenuation slope is at a maximum and this point identified as location of the diaphragm. If a determination has been made at 72 that the scout scan started in the body, then at 78 the point at another predetermined distance from the beginning of the body where the maximum slope of the PA attenuation occurs is identified. In this example, a determination is made at 78 as to the point within about 400 mm from the identified start of the body where the PA attenuation slope is at a maximum and this point identified as location of the diaphragm.

A determination also may be made as to the width of an individual projection at the diaphragm. For example, a width threshold may be used to ensure that the projection does not encompass the arms or shoulders of the portion and which may have accounted for the maximum slope determination.

After the point of the maximum slope of the PA attenuation is identified at either 76 or 78, a determination is made at 80 as to whether the oval ratio is greater than a predetermined value, in this example 0.55 (with oval ratios lower generally identifying the neck region of the person). If the oval ratio is not greater than 0.55, then at 82 a determination is made that the shoulders or neck was identified and the point where the maximum slope of the PA attenuation occurs is again determined for a predetermined additional distance, in this example, about 200 mm to about 300 mm. Thereafter, or if the oval ratio is greater than 0.55, then at 84 a determination is made as to whether the location of the maximum slope occurred at a point known to be within the scout scan, for example, based on the known length of the scout scan. If a determination is made at 84 that the point is within the scout scan, which identifies the location of the diaphragm, then at 86, based on this location and the PA attenuation at this point, the locations of other parts of the body may be identified, including, for example, the hips and other areas of interest. Additionally, the body size of the patient may be estimated by the PA attenuation value using, for example, average PA attenuation values for different size patients at the diaphragm as determined by clinical evaluations or studies. Essentially, the PA attenuation is related to the height of the person and also to intermediate distances, for example, the distance from the diaphragm to the hips. It should be noted that individual linear fitting functions may be used to estimate the distance from the diaphragm to other regions of interest, for example, other organs of interest. Further, the area from the diaphragm to the hips can be used to calculate the centering error and the bowtie selection filter used to identify the locations of other regions in the body of a person based on measurements of typical distances relative to the diaphragm, which may be based on, for example, age and gender. Such information may be determined by clinical measurement or using known charts/tables, for example, as described in "The Measure of Man & Woman", Henry Dreyfuss, 2002, or "IGRP Publication 70: Basic Anatomical & Physiological Data for Use in Radiologic Protection", published by Pergamon, 1996, both of which are incorporated by reference in their entirety herein.

If a determination is made at 84 that the point is not within the scout scan, then at 88 a determination is made as to whether this point is on the scout scan and the beginning of the head identified as described above. If the location is identified as the beginning of the head, then at 90 the locations of other parts of the body may be identified, including, for example, the eyes, shoulder and other areas of interest based on the PA attenuation as described above. If at 88 a determination is made that this point is not on the scout scan and/or not the beginning of the head, then at 92 a determination is made that no landmark can be identified for use in locating other regions within the person. An error indication (e.g., visual or audible) may be provided.

Thus, using x-ray data magnitudes, rates of change (slope) and symmetry, as well as tables or determinations of expected human anatomy (versus age, gender, size, etc.), various embodiments of the invention provide automatic determination of regions in a scanned body. For example, anatomic locations within a person may be automatically determined using a scout scan. Further, a priori protocol and patient information also may be used to improve prediction accuracy.

The automatic location of regions with an object, and more particularly, anatomic locations or regions within a person may be used in connection with other procedures. For example, the various embodiments may be used in connection with CT dose reduction for dose sensitive organs. With the locations of sensitive organs identified, the system can then lower and increase the mA respectively when over the anterior and posterior of automatically identified sensitive organ regions. Automatic identification can reduce or eliminate the need for manually marking locations on a graphic Rx display. Further, automatic identification of the trunk of a person can provide more consistent assisted patient centering and size adjusted noise index performance. Different regions (e.g., the lungs) also can be automatically identified on the graphic Rx display to minimize the need for manual identification of the region to be scanned. Automatic identification of the precise scan region can minimize the extra scan range and save patient dose and tube loading.

Additionally, regions of the anatomy that may require special compute intensive image reconstruction pre-processing correction steps may be automatically identified. Also, the effective CT dose may be calculated by automatically determining the organs that have been exposed to x-ray. The automatically identified location information, such as patient dependent anatomic locations and landmarks also may be used to automatically adjust the start or landmark position, as well as the load and unload position of a medical imaging scanner. This information further may be used to center a person in an imaging scanner based on a landmarked position or anatomical structure.

While the invention has been described in terms of various specific embodiments, those skilled in the art will recognize that the invention can be practiced with modification within the spirit and scope of the claims.

What is claimed is:

1. A method for controlling an imaging system, said method comprising:
    performing a scout scan of an object using a scanner of the imaging system;
    automatically identifying a first region based on attenuation information from the scout scan, the first region being one of within the object and or within a component of the imaging system; and
    automatically determining a location of a second region using an anatomy determination unit of the imaging system, the automatically determining being based upon a location of the first region and based upon the attenuation information from the scout scan, the second region being within the object;
    wherein said performing the scout scan includes scanning a length of the object along an examination axis of the imaging system, said automatically determining the location of the second region including determining whether an attenuation information characteristic exists within a predetermined axial distance from the first region, the axial distance being measured along the examination axis.

2. A method in accordance with claim 1 wherein the scout scan comprises an x-ray scan.

3. A method in accordance with claim 1 wherein the location of the second region is determined based upon a rate of change in attenuation and symmetry information from the scout scan.

4. A method in accordance with claim 1 wherein the object is a human and the anatomy determination unit automatically determines a location of a diaphragm of the human, the anatomy determination unit automatically determining the location of the second region within the human based on the location of the diaphragm.

5. A method in accordance with claim 1 wherein the object is a human.

6. A method in accordance with claim 1 wherein the scout scan comprises at least one of a lateral or anterior/posterior scan.

7. A method in accordance with claim 1 wherein the automatically determining the location of the second region includes using the oval ratio of the second region, the oval ratio being based upon the attenuation information of a slice of the scout scan.

8. A method for determining anatomic locations in a human scanned with a medical imaging system, said method comprising:
    performing a scout scan of the human with the medical imaging system;
    automatically determining a first anatomic location within the human using the scout scan; and
    automatically determining a second anatomic location within the human using an anatomy determination unit of the imaging system, the automatically determining the second anatomic location being based upon the first anatomic location and attenuation information of the scout scan;

wherein the first anatomic location is a diaphragm location of the human and the anatomy determination unit automatically determines the diaphragm location, the anatomy determination unit automatically determining the second anatomic location within the human based on the diaphragm location.

9. A method in accordance with claim 8 further comprising performing attenuation thresholding based on the attenuation information from the scout scan to automatically determine the first and second anatomic locations, wherein the attenuation thresholding includes comparing the attenuation information of the scout scan to a predetermined threshold.

10. A method in accordance with claim 8 wherein the medical imaging system comprises a computed tomography (CT) imaging system, the method further comprising using at least one of x-ray attenuation data magnitudes, attenuation rates of change, or symmetry information to automatically determine the anatomic locations.

11. A method in accordance with claim 8 further comprising automatically determining a location of a component of the medical imaging system, the component including a scanner table or a head holder.

12. A medical imaging system comprising:
a scanner configured to perform a scout scan that includes scanning a length of the human along an examination axis; and
an anatomy determination unit configured to automatically determine a first anatomic location within a human based on the scout scan and automatically determine a second anatomic location based upon the first anatomic location;
wherein the anatomy determination unit automatically determines the second anatomic location by determining whether an attenuation information characteristic exists within a predetermined axial distance from the first anatomic location, the predetermined axial distance being measured along the examination axis, the attenuation information characteristic including at least one of an attenuation data magnitude, a rate of change in attenuation, an oval ratio, or symmetry information.

13. The method in accordance with claim 1 wherein:
the scout scan includes a plurality of slices;
the performing the scout scan includes obtaining an object projection for each slice, the object projection comprising a set of individual detector channel measurements; and
the automatically identifying and determining includes summing the individual channel measurements to obtain a projection area (PA) for each slice.

14. The method in accordance with claim 8 wherein:
the scout scan includes a plurality of slices;
the performing the scout scan includes obtaining a patient projection for each slice, the patient projection comprising a set of individual detector channel measurements; and
the automatically determining anatomic locations includes summing the individual channel measurements to obtain a projection area (PA) for each slice.

15. The method in accordance with claim 14 wherein each projection area is represented by an attenuation value and the automatically determining anatomic locations includes automatically determining at least one anatomic location based upon a rate of change in attenuation values in a series of slices.

16. The method in accordance with claim 14 wherein the automatically determining anatomic locations within the human includes using an oval ratio of a corresponding slice, the oval ratio being determined by the PA of the corresponding slice and by a set of highest value measurements in the corresponding slice.

17. A method in accordance with claim 1 wherein the attenuation information characteristic includes at least one of an attenuation data magnitude, rate of change, oval ratio, or symmetry information.

18. A method in accordance with claim 1 wherein the automatically determining the location of the second region includes automatically identifying a dose-sensitive region, the method further comprising selectively scanning the second region including selectively reducing an x-ray dosage while scanning the location of the second region.

19. A method in accordance with claim 1 wherein the first region is within the component of the imaging system, the component including a table or a head holder that does not include the object thereon at the location of the first region.

20. A method in accordance with claim 1 wherein the locations of the first and second regions are spaced apart from each other.

21. A medical imaging system in accordance with claim 12 wherein the second anatomic location is automatically determined based upon the attenuation information from the scout scan relative to the first anatomic location.

22. A medical imaging system in accordance with claim 12 wherein the first anatomic location is a diaphragm location of the human and the anatomy determination unit automatically determines the diaphragm location, the anatomy determination unit automatically determining the second anatomic location within the human based on the diaphragm location.

23. A method in accordance with claim 1 further comprising using the location of the second region to adjust a scan position of the scanner in order to selectively scan the location of the second region.

24. A medical imaging system in accordance with claim 12, wherein a scan position of the scanner is adjusted based on the second anatomic location in order to selectively scan the second anatomic location.

* * * * *